(12) United States Patent
Park

(10) Patent No.: US 11,116,610 B2
(45) Date of Patent: Sep. 14, 2021

(54) METHOD FOR MANUFACTURING ZIRCONIA SLURRY FOR FORMING POROUS SURFACE ON ABUTMENT AND CROWN OF CERAMIC IMPLANT AND METHOD FOR MANUFACTURING IMPLANT USING THE SAME

(71) Applicant: DMAX CO., LTD., Daegu (KR)

(72) Inventor: Tae Seok Park, Seoul (KR)

(73) Assignee: DMAX CO., LTD., Daegu (KR)

( * ) Notice: Subject to any disclaimer, the term of this patent is extended or adjusted under 35 U.S.C. 154(b) by 55 days.

(21) Appl. No.: 16/679,903

(22) Filed: Nov. 11, 2019

(65) Prior Publication Data
US 2020/0268487 A1 Aug. 27, 2020

(30) Foreign Application Priority Data
Feb. 21, 2019 (KR) .................. 10-2019-0020384

(51) Int. Cl.
*A61C 13/083* (2006.01)
*A61C 5/77* (2017.01)
(Continued)

(52) U.S. Cl.
CPC .............. *A61C 13/083* (2013.01); *A61C 5/73* (2017.02); *A61C 5/77* (2017.02); *A61C 8/0012* (2013.01); *A61C 13/00* (2013.01); *A61C 13/0003* (2013.01)

(58) Field of Classification Search
USPC ...... 501/2, 41, 73; 433/9, 17, 215, 218, 206, 433/202.1, 201, 1, 222.1, 213, 223;
(Continued)

(56) References Cited

U.S. PATENT DOCUMENTS

| 5,062,798 A * | 11/1991 | Tsuge | ............... A61C 8/0012 433/201.1 |
| 6,984,261 B2 * | 1/2006 | Cummings | ....... C04B 35/62665 106/35 |

(Continued)

FOREIGN PATENT DOCUMENTS

| JP | 10-277061 A | 10/1998 |
| JP | 2013-022070 A | 2/2013 |

(Continued)

*Primary Examiner* — Lawrence Averick
(74) *Attorney, Agent, or Firm* — Novick, Kim & Lee, PLLC; Jae Youn Kim

(57) ABSTRACT

The present invention relates to a method for manufacturing a zirconia slurry for forming porous surfaces on an abutment and a crown of a ceramic implant, the method including: the zirconia pulverization step (step S10) of putting zirconia powder, carbon powder as a foaming agent, and an organic binder in a ball mill and agitating and pulverizing the zirconia, carbon powder, and organic binder to allow the mixed zirconia powder to have nanoparticles; the carbon powder oxidization step (step S20) of heating the zirconia powder mixed with the carbon powder to a temperature of 1200 to 1800° C. and oxidizing the carbon powder to a concentration of 10 to 40 wt % to allow the porous surfaces to be formed on every particle of the zirconia powder; and the degreasing step (step S30) of putting a dispersing agent and a solvent in the zirconia powder whose particles have the porous surfaces to make a zirconia solution and removing the organic binder from the zirconia powder.

6 Claims, 11 Drawing Sheets

(51) Int. Cl.
*A61C 5/73* (2017.01)
*A61C 8/00* (2006.01)
*A61C 13/00* (2006.01)

(58) Field of Classification Search
USPC .................................. 106/35, 38.22; 264/16
See application file for complete search history.

(56) References Cited

U.S. PATENT DOCUMENTS

| | | | |
|---|---|---|---|
| 9,913,476 B2* | 3/2018 | Agrawal | A61K 8/25 |
| 10,358,856 B2* | 7/2019 | Tomlinson | E05D 15/0626 |
| 2004/0152034 A1* | 8/2004 | Cummings | C04B 35/645 |
| | | | 433/8 |
| 2007/0003753 A1* | 1/2007 | Asgari | A61L 27/446 |
| | | | 428/315.5 |
| 2009/0098511 A1* | 4/2009 | Zhang | A61C 13/0001 |
| | | | 433/201.1 |
| 2010/0016989 A1* | 1/2010 | Lyngstadaas | A61L 27/56 |
| | | | 623/23.72 |
| 2015/0216637 A1* | 8/2015 | Narumi | A61C 8/0012 |
| | | | 433/8 |
| 2016/0135470 A1* | 5/2016 | Agrawal | A01N 25/12 |
| | | | 424/404 |

FOREIGN PATENT DOCUMENTS

| | | |
|---|---|---|
| KR | 10-0902328 B1 | 6/2009 |
| KR | 10-2009-0070982 A | 7/2009 |
| KR | 10-2011-0112740 A | 10/2011 |
| KR | 10-1251888 B1 | 4/2013 |
| KR | 10-1913589 B1 | 10/2018 |
| KR | 10-1973729 B1 | 4/2019 |

* cited by examiner

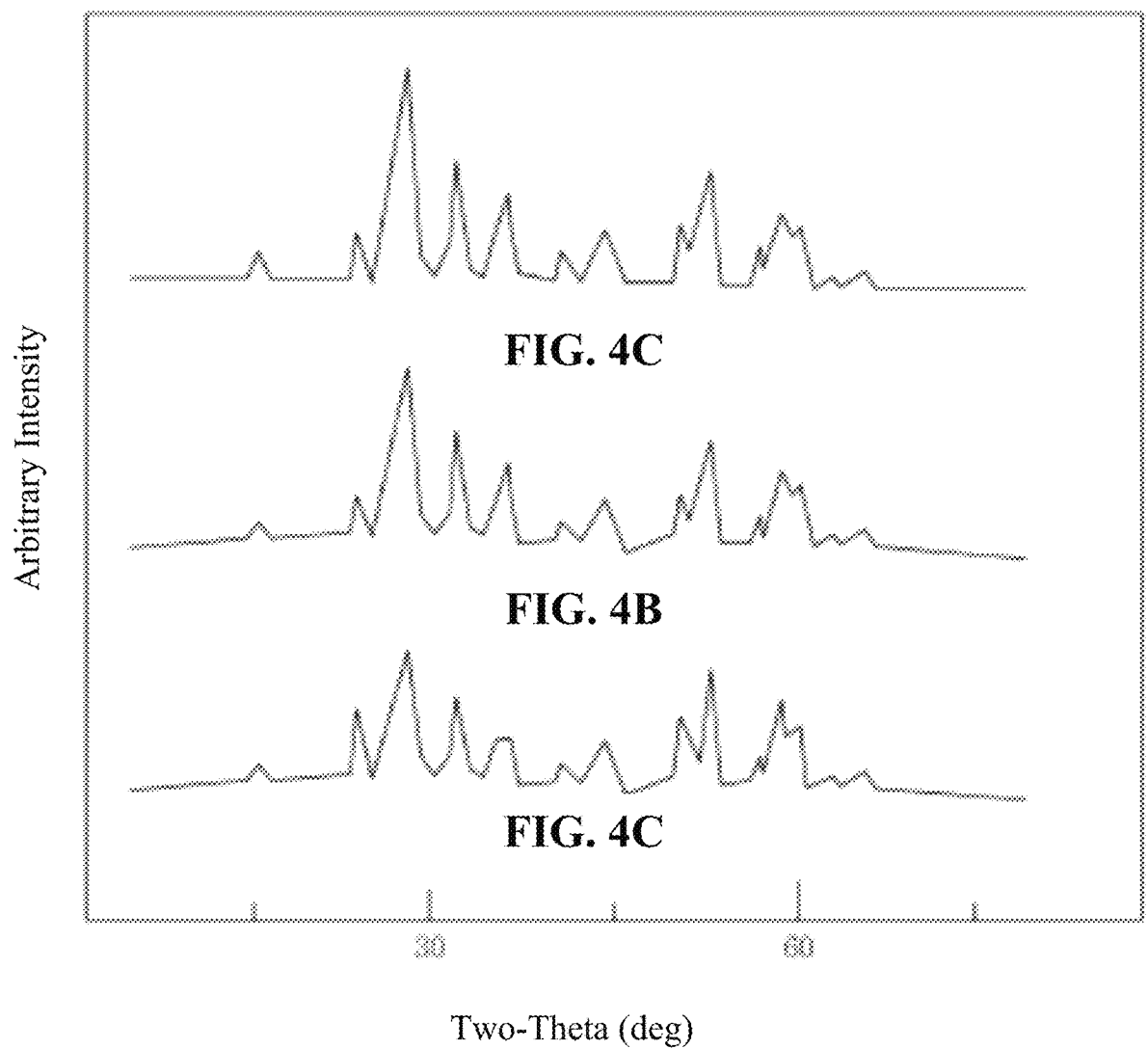

METHOD FOR MANUFACTURING ZIRCONIA SLURRY FOR FORMING POROUS SURFACE ON ABUTMENT AND CROWN OF CERAMIC IMPLANT AND METHOD FOR MANUFACTURING IMPLANT USING THE SAME

CROSS REFERENCE TO RELATED APPLICATION OF THE INVENTION

The present application claims the benefit of Korean Patent Application No. KR10-2019-0020384 filed in the Korean Intellectual Property Office on Feb. 21, 2019, the entire contents of which are incorporated herein by reference.

BACKGROUND OF THE INVENTION

Field of the Invention

The present invention relates to a method for manufacturing a zirconia slurry for forming porous surfaces on an abutment and a crown of a ceramic implant and a method for manufacturing an implant using the same, and more particularly, to a method for manufacturing a zirconia slurry for forming porous surfaces on an abutment and a crown of a ceramic implant and a method for manufacturing an implant using the same that are capable of manufacturing the zirconia slurry having nanoparticles through a ball mill in more improved way than the existing way, allowing the manufactured zirconia slurry to be applied and dried on specific objects to form the porous surfaces thereon, thereby greatly improving a coupling force between the abutment and the crown or between a laminate and a patient's tooth, and optimizing bio convergence of the implant itself to allow fibrous tissue of a patient's alveolar bone to enter the inside of the implant and to grow there, thereby improving and inducing contacted surfaces between the implant and bone tissues.

Background of the Related Art

Typically, dental implant surgery is a procedure that replaces damaged or missing teeth with artificial teeth, and it is classified into implant surgery for the missing teeth and laminate surgery for the damaged teeth.

In detail, the implant surgery is one of dental treatments for planting an implant body adequate to a living body into an alveolar bone with a missing tooth to restore and induce functions like a natural tooth, and generally, the implant includes a fixture made of a titanium material and planted on an alveolar bone, an abutment insertedly fixed to the fixture to induce an insertion direction of a crown and coupling with the crown, the crown having a shape of a tooth in such a manner as to be insertedly placed on an end of the abutment exposed to the top of the alveolar bone, and a coupling member for preventing the crown inserted into the abutment from escaping from the abutment.

On the other hand, the laminate surgery is a procedure with an esthetic purpose that deletes only the labial surface of an enamel of a front tooth to the minimum, makes a porcelain prosthesis, and attaches the porcelain prosthesis to the labial surface through a composite resin. Unlike the existing prosthesis removing a large amount of a tooth, the laminate is attached to the damaged tooth, so that a surgery cost is low, side effects do not almost exist, and there is no metal in the laminate to thus provide excellent natural feeling or transparency in an aesthetic view.

The most important subject of the implant surgery is to allow the artificial tooth provided for the patient to be solidly kept there even if long time passes, and in dental medical industries, accordingly, many endeavors have been made to suggest technology capable of satisfying such subject of the implant surgery.

For example, a conventional technology related to an implant is disclosed in Korean Patent Application Laid-open No. 2007-0139163 entitled "Implant for artificial tooth for preventing screw loosening", and in such conventional technology, the implant includes a fixing screw having a screw portion coupled to a fixture in such a manner as to pass through a screw insertion hole formed on an abutment and a head portion formed on top of the screw portion in such a manner as to be locked onto a head seating portion protruding inward from the screw insertion hole and loosening preventing means made of an elastically deformed elastic material in such a manner as to be located between the head portion and the head seating portion, at the time when the fixing screw is fastened, to firmly couple the head portion and the head seating portion to each other.

However, the conventional technology is just a technology in which a washer is used at the time when a bolt is fastened to a metal part to prevent the bolt from being drawn, without intention, so that it can be expected well even by a person who is not skilled in the art.

On the other hand, one example of the laminate technology is disclosed in Korean Patent No. 10-1913589 entitled "Method for manufacturing laminate prosthesis".

The conventional method includes the steps of making a wax pattern to form an outer shape of a laminate (veneer), making a mold by means of the wax pattern, burning out the mold at a high temperature, and thermally pressurizing the ceramic veneer against the mold, and especially, since an added injection line is formed even on the mold by means of an added injection line formed on the surface of the wax pattern, a ceramic ingot in the thermal pressurization evenly flows into the mold, thereby making the ceramic veneer having a thickness less than 0.3 mm.

However, the conventional technology is just a method that is capable of manufacturing the ceramic veneer to a relatively thin thickness, so that there is no improvement in durability of the veneer and a bonding force between the veneer and a surgery tooth.

A variety of methods have been developed to improve a coupling force between the components of the implant, but unfortunately, there is no technology having functions applicable actually to a patient's tooth.

Therefore, there is a definite need for the development of a new implant surgery method for improving the osseointegration of an implant into a patient's alveolar bone and for increasing a coupling force between an abutment and a crown or between a veneer and a tooth, thereby achieving permanent surgery.

SUMMARY OF THE INVENTION

Accordingly, the present invention has been made in view of the above-mentioned problems occurring in the related art, and it is an object of the present invention to provide a method for manufacturing a zirconia slurry for forming porous surfaces on an abutment and a crown of a ceramic implant and a method for manufacturing an implant using the same that are capable of allowing the zirconia slurry to be applied to coupled surfaces of the components constituting the implant to form the porous surfaces thereon, so that a coupling force between the components can be drastically increased.

It is another object of the present invention to provide a method for manufacturing a zirconia slurry for forming porous surfaces on an abutment and a crown of a ceramic implant and a method for manufacturing an implant using the same that are capable of applying the zirconia slurry having nanoparticles to be applied to the components constituting the implant to form the porous surfaces thereon, thereby improving a coupling force between the components of the implant.

It is yet another object of the present invention to provide a method for manufacturing a zirconia slurry for forming porous surfaces on an abutment and a crown of a ceramic implant and a method for manufacturing an implant using the same that are capable of allowing the components of the implant to have different porous surface distribution flows from each other according to application directions of the zirconia slurry, thereby improving friction areas and coefficients of the components to optimize a coupling force between the components of the implant.

To accomplish the above-mentioned objects, according to one aspect of the present invention, there is provided a method for manufacturing a zirconia slurry for forming porous surfaces on an abutment and a crown of a ceramic implant, the method including: the zirconia pulverization step of putting zirconia, carbon powder as a foaming agent, and an organic binder in a ball mill and agitating and pulverizing the zirconia, the carbon powder, and the organic binder to allow the zirconia mixture to have nanoparticles; the carbon powder oxidization step of heating the zirconia mixture mixed with the carbon powder to a temperature of 1200 to 1800° C. and oxidizing the carbon powder to a concentration of 10 to 40 wt % to allow the porous surfaces to be formed on every particle of the zirconia mixture; and the degreasing step of putting a dispersing agent and a solvent in the zirconia mixture having the porous surfaces to make a zirconia solution and removing the organic binder from to the zirconia mixture.

According to the present invention, desirably, the zirconia pulverization step includes: the powder preparation step of selecting one from zirconium(IV) acetate hydroxide, zirconium nitrate, and zirconium chloride and pulverizing the selected zirconia material by means of the ball mill; the distilled water preparation step of adding double distilled water having a deionized process in an internal space of an autoclave used for hydrothermal synthesis; and the powder dissolution step of adjusting a temperature of the autoclave to which the distilled water is added to a temperature of 90 to 100° C., putting the zirconia powder and a precipitation agent into the autoclave, and dissolving the zirconia powder for two to four hours.

According to the present invention, desirably, the precipitation agent is one selected from NaOH and KOH.

To accomplish the above-mentioned objects, according to another aspect of the present invention, there is provided a method for manufacturing an implant with the zirconia slurry manufactured according to one aspect of the present invention so as to form porous surfaces on an abutment and a crown of the implant, the method including: the slurry preparation step of putting the zirconia slurry in a storage container; the component machining step of allowing an inner diameter of the crown to be more enlarged by 0.01 to 0.1 mm than a head of the abutment to ensure a spare space on a coupled surface between the crown and the abutment; the slurry application step of applying the zirconia slurry to an inner periphery of the crown and the head of the abutment; the slurry drying step of allowing the crown and the abutment to which the zirconia slurry is applied to be dried at a temperature of 120 to 150° C. for 10 to 20 minutes; and the component coupling step of press-fitting the head of the abutment to the inner periphery of the crown to allow the abutment and the crown fitted to each other to be coupled to a fixture planted into a patient's alveolar bone.

To accomplish the above-mentioned objects, according to yet another aspect of the present invention, there is provided a method for manufacturing a laminate with the zirconia slurry manufactured according to one aspect of the present invention, the method including: the slurry preparation step of putting the zirconia slurry in a storage container; the component machining step of putting a melted ceramic material into a mold to make a veneer; the slurry application step of applying the zirconia slurry to an inner surface of the veneer; the slurry drying step of allowing the veneer to which the zirconia slurry is applied to be dried at a temperature of 120 to 150° C. for 10 to 20 minutes; and the component coupling step of applying a composite resin to a patient's tooth to attach the veneer to the tooth.

According to the present invention, desirably, the ball mill for pulverizing the zirconia powder comprises a machining container and at least one or more agitating balls having different diameters disposed in the machining container, and the agitating balls have porous surfaces to allow the zirconia powder to be machined to nanoparticle sizes.

According to the present invention, desirably, at the slurry application step the zirconia slurry is applied toward a lower side of the crown from an inner upper periphery of the crown, thereby being enlargedly distributed toward the lower side of the crown from the inner upper periphery of the crown, and the zirconia slurry is applied toward the upper side of the abutment from the bottom of the head of the abutment, thereby being enlargedly distributed toward the upper side of the abutment from the bottom of the head of the abutment, so that the application flows of the zirconia slurry to the abutment and the crown are in reverse directions to each other.

BRIEF DESCRIPTION OF THE DRAWINGS

The above and other objects, features and advantages of the present invention will be apparent from the following detailed description of the embodiments of the invention in conjunction with the accompanying drawings, in which:

FIGS. 4A-4C are graphs showing changes in the fine structures of the zirconia powder to the kinds of the zirconium precursors according to the present invention;

DETAILED DESCRIPTION OF THE EMBODIMENTS

Figure 1:
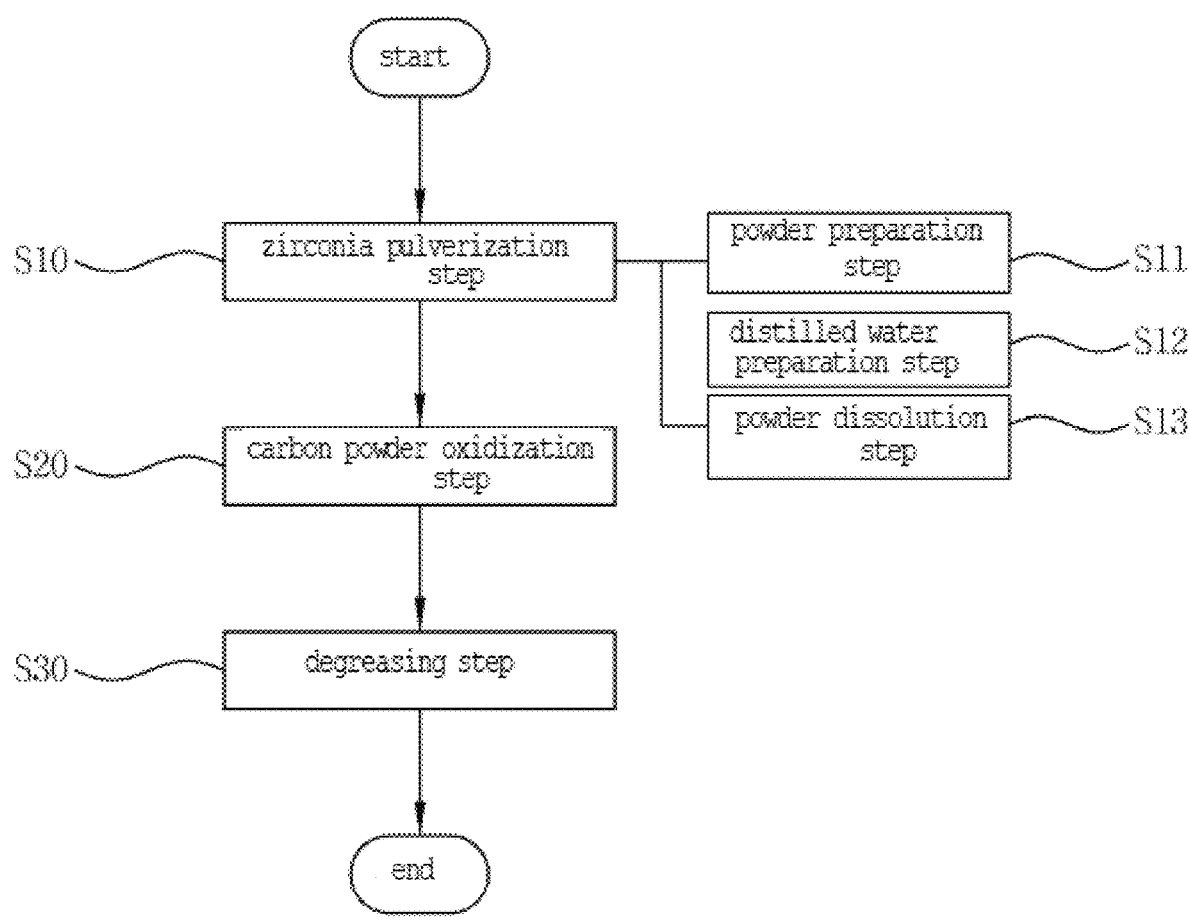
FIG. 1 is a flowchart showing a method for manufacturing a zirconia slurry for forming porous surfaces on an abutment and a crown of a ceramic implant according to the present invention.

Hereinafter, a configuration, operations, and effects of the present invention will be disclosed with reference to the attached drawings.

Objects, characteristics and advantages of the present invention will be more clearly understood from the detailed description as will be described below and the attached drawings. Before the present invention is disclosed and described, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. The corresponding parts in the embodiments of the present invention are indicated by corresponding reference numerals.

According to the present invention, above all, there are provided a method for manufacturing a zirconia slurry for forming porous surfaces on an abutment and a crown of a ceramic implant and a method for manufacturing an implant with the same that are capable of manufacturing the zirconia slurry having nanoparticles through a ball mill in more improved way than the existing way, allowing the manufactured zirconia slurry to be applied and dried on specific objects to form the porous surfaces thereon, thereby greatly improving a coupling force between the abutment and the crown or between a laminate and a patient's tooth, and optimizing bio convergence of the implant itself to allow fibrous tissue of a patient's alveolar bone to enter the inside of the implant and to grow there, thereby improving and inducing contacted surfaces between the implant and hone tissues.

FIG. 1 is a flowchart showing a method for manufacturing a zirconia slurry for forming porous surfaces on an abutment and a crown of a ceramic implant according to the present invention.

As shown in FIG. 1, a zirconia slurry suggested in the present invention is a mixture of zirconia powder pulverized to nanoparticles by means of a ball mill, water, and a foaming agent made of carbon powder.

So as to finely apply porosity to surfaces of the zirconia slurry, particularly, it is important to add an organic binder, a dispersing agent, and a solvent to the mixture, and at this time, the zirconia slurry is most desirably produced by mixing 25 to 45% by weight of zirconia powder, 8 to 15% by weight of carbon powder, 1 to 5% by weight of a binder, 1 to 5% by weight of a dispersing agent, and 45 to 50% by weight of a solvent.

Experimental data on the mixing ratios of the zirconia slurry of the present invention will be suggested below.

1. Viscosity Measurement According to Weights of Zirconia Powder and Solvent

Sample 1: mixed with 10 to 20% by weight of zirconia powder and 80 to 90% by weight of a solvent Sample 2: mixed with 30 to 40% by weight of zirconia powder and 60 to 70% by weight of a solvent Sample 3: mixed with 50 to 60% by weight of zirconia powder and 40 to 60% by weight of a solvent

TABLE 1

Viscosity Measurement

| | Item | Standard No. | Standard | Sample 1 | Sample 2 | Sample 3 |
|---|---|---|---|---|---|---|
| | Viscosity | ASTM D2196 | 220 McP | 127.8 McP | 216.9 McP | 321.5 McP |
| | Kinematic viscosity | ASTM D445 (ISO 3104) | 18700 cSt | 11205.2 cSt | 19850.7 cSt | 35750.1 cSt |
| | Viscosity index | ASTM D2270 | 120000 cSt | 7865.7 cSt | 11955.5 cSt | 18752.2 cSt |
| Inherent Viscosity | Inherent viscosity | ASTM D4603-03 | 75.5% | 52.7% | 70.8% | 89.2% |
| | Intrinsic viscosity | ASTM D1795 | 25% | 28% | 24% | 32% |

<Viscosity Comparison Table According to the Mixing Ratios of the Zirconia Powder and the Solvent>

According to the present invention, experiments for viscosity, kinematic viscosity, and inherent viscosity are carried out, and so as to measure the viscosity, liquid samples with low to high viscosities are measured at a given temperature through a Brookfield rotational or vibrational viscometer. So as to measure the kinematic viscosity, further, liquid samples are measured at a given temperature through falling time of a Cannon-Fenske or Ubbelohde (capillary) viscometer, and so as to measure the inherent viscosity, solid samples are melted with a solvent to a given concentration and their inherent viscosity are measured at a given temperature through Ubbelohde (capillary) viscometer.

As appreciated from Table 1, the zirconia slurry, which is provided to enhance a coupling force between an abutment and a crown, most desirably has the viscosity of 220 McP, kinematic viscosity of 18700 cSt, inherent viscosity of 75.5%, and intrinsic viscosity of 25%, and if the zirconia slurry has such standard values, the abutment and the crown to which the zirconia slurry is applied can be most perfectly coupled to each other. Even in plastic and sintering processes for the abutment and the crown to which the zirconia slurry is applied, further, zirconia particles can remain completely, thereby achieving optimal objects of the present invention.

The sample having the closest values to the standard values is the sample 2 of the present invention. As appreciated from the measurement results, accordingly, the zirconia slurry is made by mixing 30 to 40% by weight of zirconia powder and 60 to 70% by weight of a solvent so as to provide the most desirable concentration thereof.

1. Porous Surface Measurement According to Weights of Zirconia Powder and Carbon Powder Sample 1: mixed with 80 to 90% by weight of zirconia powder and 10 to 20% by weight of carbon powder
Sample 2: mixed with 60 to 70% by weight of zirconia powder and 30 to 40% by weight of carbon powder
Sample 3: mixed with 30 to 40% by weight of zirconia powder and 60 to 70% by weight of carbon powder

TABLE 2

| | | Porous surface measurement | | | |
|---|---|---|---|---|---|
| Item | Standard No. | Standard | Sample 1 | Sample 2 | Sample 3 |
| Pore size | — | 0.5 nm | 0.03 nm | 0.47 nm | 0.66 nm |
| Pore density | — | 0.85 nm | 1.35 nm | 0.91 nm | 0.7 nm |
| Surface roughness | R max | 0.85 nm | 0.35 nm | 0.81 nm | 1.25 nm |
| | R2 | 0.72 nm | 0.42 nm | 0.70 nm | 0.92 nm |
| | Ra | 0.45 nm | 0.15 nm | 0.42 nm | 0.58 nm |
| Tensile strength | ASTM D 638 | 0.05 nm | 0.02 nm | 0.04 nm | 0.08 nm |
| Friction coefficient | ASTM D1630 | 0.5 mm | 0.2 mm | 0.4 mm | 0.4 mm |
| Elastic force | ASTM D 790 | 3.2% | 1.8% | 3.1% | 3.4% |

<Porous Surface Measurement Table According to the Mixing Ratios of the Zirconia Powder and the Carbon Powder>

So as to optimize the coupling force between the abutment and the crown, the surfaces of the particles of the zirconia slurry have to be rough, thereby providing excellent performance in the coupling force, and also, densities between the particles of the zirconia slurry have to be tight and firm.

As the number of pores is increased on the surfaces of the powder, the strength of the powder itself becomes lowered. So as to optimize the surface roughness in a state where the strength of the zirconia powder is kept to a maximum degree, as appreciated from Table 2, the zirconia powder most desirably has a pore size of 0.5 nm, a pore density of 0.85 nm, a maximum roughness height of 0.85 nm, ten point average roughness of 0.72 nm, and center line average roughness of 045 nm. The zirconia powder having such pore size and density maintains tensile strength of 0.05 nm, friction coefficient of 0.5 mm, and elastic force of 3.2%, so that even if it is applied to the implant, it can keep its functions perfectly.

The sample having the closest values to the standard values is the sample 2 of the present invention. As appreciated from the measurement results, accordingly, the zirconia slurry is made by mixing 60 to 70% by weight of zirconia powder and 30 to 40% by weight of carbon powder so as to form the most desirable porous surface.

3. Porous Surface Experiments According to the Mixing Ratios of an Organic Binder and a Dispersing Agent The organic binder serves as an adhesive for binding the zirconia powder, and the dispersing agent serves to remove the organic binder remaining after the zirconia powder binds.

If a content of the organic binder is large, of course, the viscosity of the zirconia powder is very high so that it is hard to perform uniform agitation, and accordingly, the agitation of the mixture is finished with a lot of masses. If a content of the organic binder is small, contrarily, cohesion of the powder is not made well, thereby making it impossible to use the mixture as the zirconia slurry.

If a content of the dispersing agent is excessive, the dispersing agent neutralizes the organic binder binding the zirconia powder as well as the organic binder unnecessary, thereby causing the mixture dough to be loosened, and if a content of the dispersing agent is less than a desirable content thereof, the viscosity of the zirconia powder becomes high, thereby making it to perform uniform agitation.

Accordingly, the zirconia slurry in the present invention has to be made by mixing 25 to 45% by weight of the zirconia powder, 8 to 10% by weight of the carbon powder, 1 to 5% by weight of the binder, 1 to 5% by weight of the dispersing agent, and 45 to 50% by weight of the solvent.

According to the present invention, there is provided a method for manufacturing the zirconia slurry for forming porous surfaces on an abutment and a crown of a ceramic implant, the method includes: the zirconia pulverization step (step S10) of putting zirconia, carbon powder as a foaming agent, and an organic binder in a ball mill and agitating and pulverizing the zirconia, the carbon powder, and the organic binder; the carbon powder oxidization step (step S20) of heating the zirconia mixture mixed with the carbon powder to a temperature of 1200 to 1800° C. and oxidizing the carbon powder to a concentration of 10 to 40 wt % to allow the porous surfaces to be formed on every particle of the zirconia mixture; and the degreasing step (step S30) of putting a dispersing agent and a solvent in the zirconia mixture having the porous surfaces to make a zirconia solution and removing the organic binder from to the zirconia mixture.

At the zirconia pulverization step (step S10), the zirconia put in the ball mill is pulverized to the form of powder, and as the zirconia powder is pulverizedly agitated with the carbon powder and the organic binder, the zirconia powder repeatedly bind together to finally provide the zirconia mixture having nanoparticles.

On the other hand, the zirconia slurry of the present invention has porous surface roughness so that it can improve a coupling force between components constituting an implant. So as to apply the porous surface roughness to the zirconia slurry, the carbon powder is mixed at the zirconia pulverization step (at step S10) to generate foams from the zirconia mixture through continuous agitation.

At the carbon powder oxidization step (step S20), the zirconia mixture from which the foams are generated is heated to a predetermined temperature and the carbon powder as the foams is oxidized to allow porous surfaces to be formed on the zirconia mixture. In this case, the zirconia mixture is heated most desirably to a temperature of 1200 to 1800° C. to oxidize the carbon powder to a concentration of 10 to 40 wt %, thereby producing the most desirable surface roughness on the surfaces of the zirconia mixture.

According to the present invention, further, a technology for freely machining a degree of roughness of the porous surfaces on the zirconia slurry is suggested.

Control for the roughness of the porous surfaces on the zirconia slurry is determined according to kinds of zirconia and powder machining methods of the corresponding zirconia.

A method for machining the zirconia to the form of powder, so as to freely machine a degree of roughness of the porous surfaces formed on the particles of the zirconia slurry, includes: the powder preparation step (step S11) of selecting a zirconia material which can be machined to nanoparticles from various kinds of zirconia materials and pulverizing the selected zirconia material by means of the ball mill; the distilled water preparation step (step S12) of adding double distilled water having a deionized process in an internal space of an autoclave used for hydrothermal synthesis; and the powder dissolution step (step S13) of adjusting a temperature of the autoclave to which the distilled water is added to a temperature of 90 to 100° C., putting the zirconia powder and a precipitation agent into the autoclave, and dissolving the zirconia powder for two to four hours.

The method for machining zirconia to the form of powder largely includes a solid phase method, a solution method, and a vaporization method, but the present invention adopts the solution method having a manufacturing cost lower than the solid phase method and the vaporization method, while easily making the zirconia powder having high purity and manufacturing the zirconia slurry having a uniform composition and a shape and size controlled.

In such solution method, starting materials and synthesis methods can be varied to manufacture spherical, rod-type, plate-type, and acicular powder, and the powder can have particles from several nanometers nm to several micrometers μm in size.

According to the present invention, in the solution method, hydrothermal synthesis which can machine the shape and size of the powder most conveniently and finely is adopted, and an experimental procedure of obtaining zirconia powder having the most excellent particle sizes in the zirconia powder manufacturing process using the hydrothermal synthesis is described below.

According to the present invention, the autoclave used for the hydrothermal synthesis is a device having a heat resistance temperature of about 260 to 270° C., a maximum capacity of 2 L, a maximum pressure of 20 Kg/cm$^2$, and a Teflon liner mounted at the inside thereof, and performs agitation at the inside thereof.

The zirconia material used in the experiment of the present invention is one selected from zirconium(IV) acetate hydroxide, zirconium nitrate, and zirconium chloride.

The precipitation agent used in the experiment of the present invention is one selected from NaOH and KOH.

The solvent used in the experiment of the present invention is double distilled water having deionization.

The experiment of the present invention was carried out by putting one selected from zirconium(IV) acetate hydroxide, zirconium nitrate, and zirconium chloride and one selected from NaOH and KOH into the autoclave, by adding the solvent to the respective mixtures and by allowing hydrothermal synthesis reaction temperatures of 100, 150 and 200° C., reaction time of 4, 8, 12 and 24 hours, and precipitation agent concentrations of 0.1, 1, 2, and 5 M to be differently applied to the respective mixtures to make the zirconia powder.

So as to recognize characteristics of the zirconia powder according to machining variables in the experiment of the present invention, SEM/EDS observations, X-ray diffraction analysis, and specific surface area analysis were carried out. The SEM/EDS observations were performed by observing the shapes, fine structures and particle sizes of metal oxide nanopowder manufactured through a scanning electron microscope (FE-SEM/EDS, SUPRA 40, Carl Zeiss Co., Ltd, Germany). A small amount of the sample was taken and dispersed, and next, it was dried on an aluminum plate to allow Au to be deposited for five minutes. After that, the sample powder was vacuumed and observed at 15 V. Also, the components of the sample powder were analyzed through the EDS analysis.

The X-ray diffraction analysis was performed by analyzing changes in crystalline phases of metal oxide nanopowder manufactured through X-ray diffraction (XRD, D/MAX 2500-V/PC, Rigaku Co., Ltd, Japan). At this time, the X-rays were made by monochromating CuKα rays generated at 40 kV and 30 mA through a Ni filter and had a measurement range from 10 to 70°. The crystalline phases were checked with JCPDS (Joint Committee of Powder Diffraction Standard).

The specific surface area analysis was performed by testing dried powder at a temperature of 100° C. for 12 hours through a specific surface area analyzer (BET, Autosorb-1, Quantachrom Co., Ltd, USA) so as to check a specific surface area of metal oxide nanopowder manufactured. A pre-treatment of the sample was performed at a temperature of 200° C. for three hours, while helium gas was being purged thereto so as to remove the remaining organic substances and impurities from the sample, and carrier gas at the measurement was N2. So as to obtain surface area data, total 55 points were measured on the adsorption and desorption of the N2 gas in a relative pressure (P/Po) range of 0.0 to 1.0.

A process of selecting the zirconia material at the powder preparation step (S11) is the same as a first embodiment as will be described below.

First Embodiment

Characteristics of Zirconia Powder According to Zirconia Materials

So as to check influences of zirconium precursors as starting materials, zirconium acetate, zirconium nitrate, and zirconium chloride were used, and a 3M KOH solution as the precipitation agent was added. Next, the hydrothermal synthesis for the mixture was carried out at a temperature of 200° C. for eight hours.

In FIGS. 4A-4C, FIG. 4A is zirconium acetate, FIG. 4B is zirconium nitrate, and FIG. 4C is zirconium chloride. Through the first embodiment, all of the zirconia powder FIGS. 4A-4C are synthesized to monoclinic phases, and as appreciated from the graph, if the zirconium chloride is used as the precursor, the XRD peak intensity of the zirconium chloride becomes lower and broader than those of the zirconium acetate and the zirconium nitrate. If the zirconium chloride is used as the precursor, in detail, the crystal sizes of the zirconia powder are smaller than those of the zirconia powder at the time when the zirconium acetate or zirconium nitrate is used as the precursor.

In case of the synthesized powder with the zirconium chloride, especially, rod type particles having a width of 20 to 30 nm and a length of 50 to 100 nm are produced, and in case of the synthesized powder with the zirconium nitrate or zirconium acetate, particles having a width of about 20 to 30 nm and a length of 80 to 100 nm are produced. If the different zirconium precursors are synthesized under the same conditions as each other, accordingly, there are no big differences when compared with other reaction conditions, but if the zirconium chloride is used as the zirconium precursor, the synthesized powder has the smallest particle sizes.

As a result, the zirconia powder is made by selecting one of zirconium(IV) acetate hydroxide, zirconium nitrate, and zirconium chloride, but according to the present invention, most desirably, the zirconium chloride having the smallest particle sizes among them is used.

The zirconia powder having fine structures can be made, while a concentration of KOH is being adjusted, by using the double distilled water having the deionization at the distilled water preparation step (S12), as will be described in a second embodiment.

Second Embodiment

Characteristics of Zirconia Powder According to Precipitation Agents

So as to check the fine structures and crystalline phases of the zirconia powder according to kinds and concentrations of precipitation agents, a reaction temperature was fixed to 200° C., reaction time was fixed to 8 h, and KOH and NaOH as the precipitation agents were used, while their concentrations were being changed to 0.1, 1, 2, and 5M, thereby making respective zirconia powder.

Figures 5A, 5B, 5C, 5D:
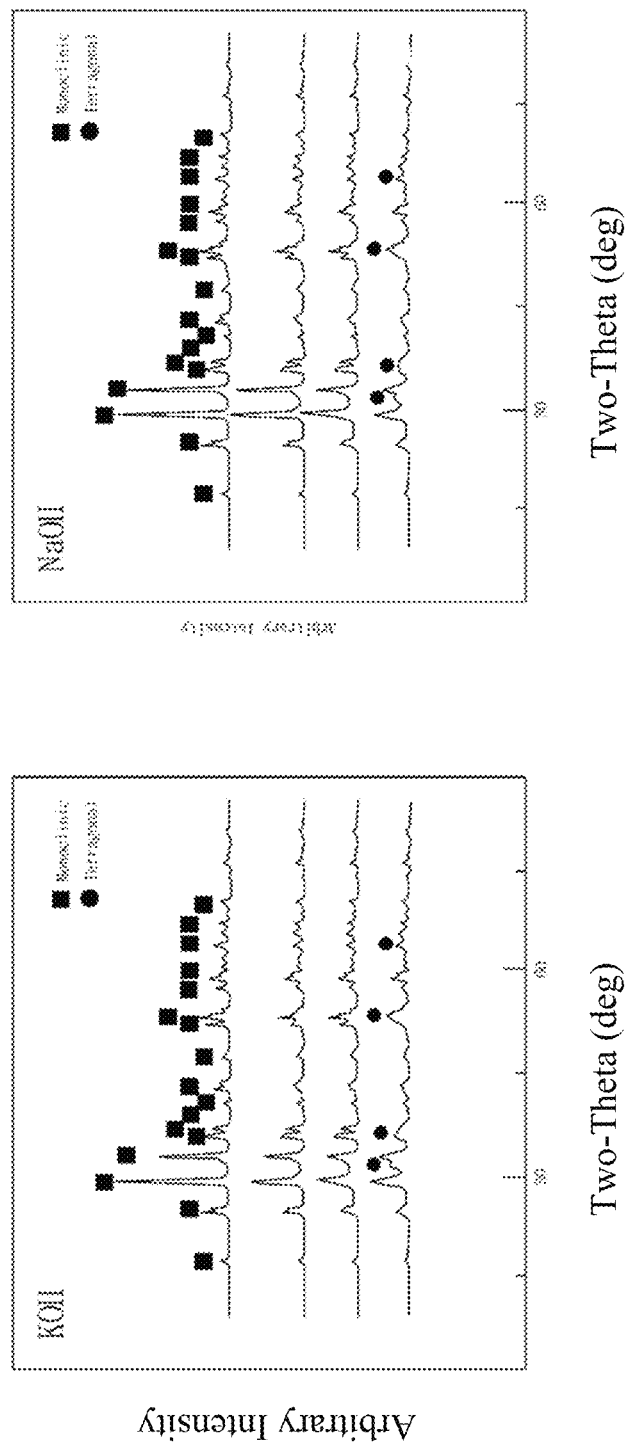
FIGS. 5A-5D are graphs showing changes in the fine structures of the zirconia powder to the kinds of the precipitation agents according to the present invention.

In FIGS. 5A-5D, FIG. 5A is a concentration of 0.1 M of a precipitation agent, FIG. 5B is that of 1 M, FIG. 5C is that of 2 M, and FIG. 5D is that of 5 M. The powder to which the 0.1 M KOH is synthesized has both of tetragonal phases and monoclinic phases, and the powder to which the 1 to 5 M KOH is synthesized has only monoclinic phases. As appreciated from the graph, the higher the concentration of the precipitation agent is, the bigger the particle sizes are.

In the same manner as above, the powder to which the 0.1 M NaOH is synthesized has both of tetragonal phases and monoclinic phases, and the powder to which the 1 to 5 M NaOH is synthesized has only monoclinic phases. As appreciated from the graph, the higher the concentration of the precipitation agent is, the bigger the particle sizes are. When KOH is compared with NaHO, however, the particle sizes of the zirconia powder with the KOH are changed more finely than those with the NaOH.

As a result, the KOH and NaOH can be selectively used as the precipitation agent, but according to the present invention, most desirably, the KOH, which makes the zirconia powder have the smallest particle sizes, is used.

The selection of a temperature and time of the autoclave at the powder dissolution step (S13) is the same as will be described in a third embodiment.

Third Embodiment

Characteristics of Zirconia Powder According to Reaction Temperatures and Time

The zirconia powder was made with zirconium chloride as a zirconium precursor through a hydrothermal process, and after 0.1 M KOH was added to the zirconia powder, the zirconia powder was synthesized with reaction temperatures of 100, 150 and 200° C. and reaction time of 4, 8, 12 and 24 h so as to check the fine structures and crystalline phases thereof according to the reaction temperatures and time.

Changes in the fine structures of the zirconia powder according to reaction temperatures are indicated.

Figures 6A, 6B, 6C, 6D:
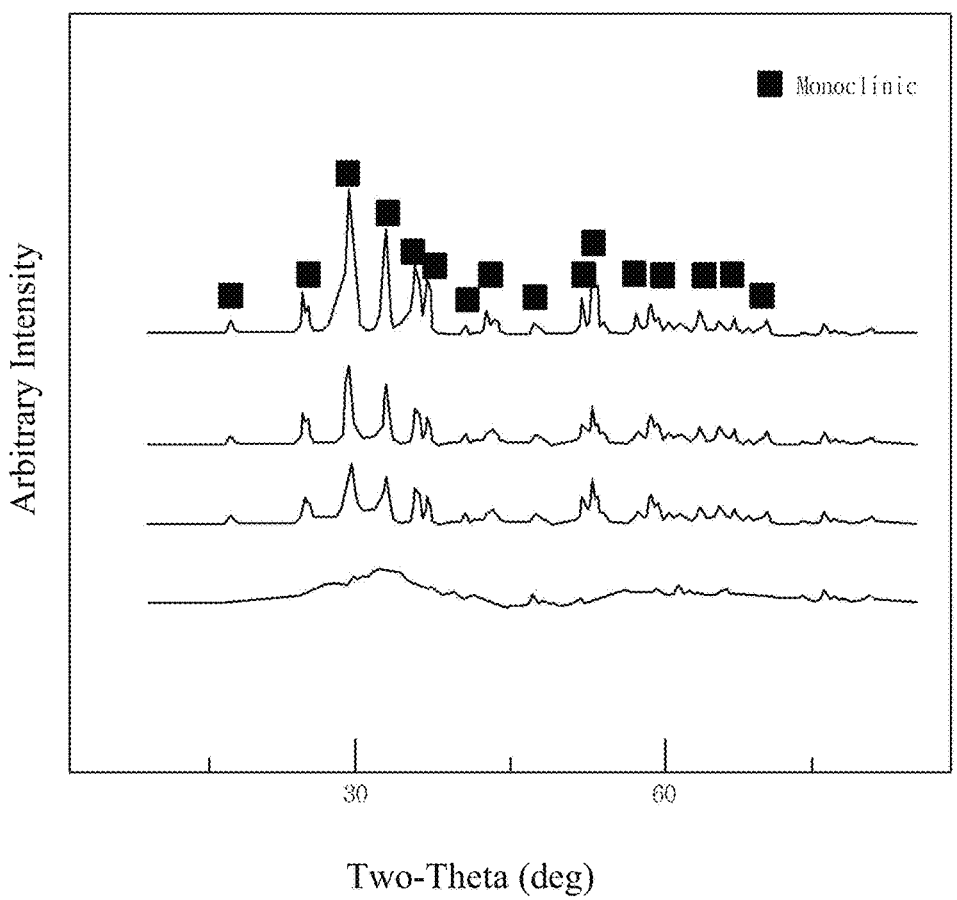
FIGS. 6A-6C are graphs showing changes in the fine structures of the zirconia powder to reaction temperatures according to the present invention.

In FIGS. 6A-6C, FIG. 6A is a temperature of 100° C., FIG. 6B is that of 150° C., and FIG. 6C is that of 200° C. If the zirconia powder is synthesized at a reaction temperature of 100° C., it has tetragonal phases, and spherical powder particles having sizes of about 10 nm are observed. Contrarily, if the zirconia powder is synthesized at a reaction temperature of 150° C., it has both of tetragonal phases and monoclinic phases, and irregular powder particles having sizes of about 20 to 50 nm are observed. Also, if the zirconia powder is synthesized at a reaction temperature of 200° C., it has monoclinic phases, and rod type of regular powder particles having widths of 30 to 50 nm and sizes of about 100 to 150 nm are observed. As appreciated from the graph, if the temperature of the hydrothermal synthesis becomes low, the spherical tetragonal phases having small particle sizes are synthesized, and contrarily, if the temperature of the hydrothermal synthesis becomes high, the rod type monoclinic phases having relatively large particle sizes are synthesized.

As a result, reaction temperatures of 100 to 200° C. can be selectively used, but according to the present invention, most desirably, the reaction temperature of 90 to 100° C., which makes the zirconia powder have the smallest particle sizes, is selected.

Figures 7A, 7B, 7C, 7D:
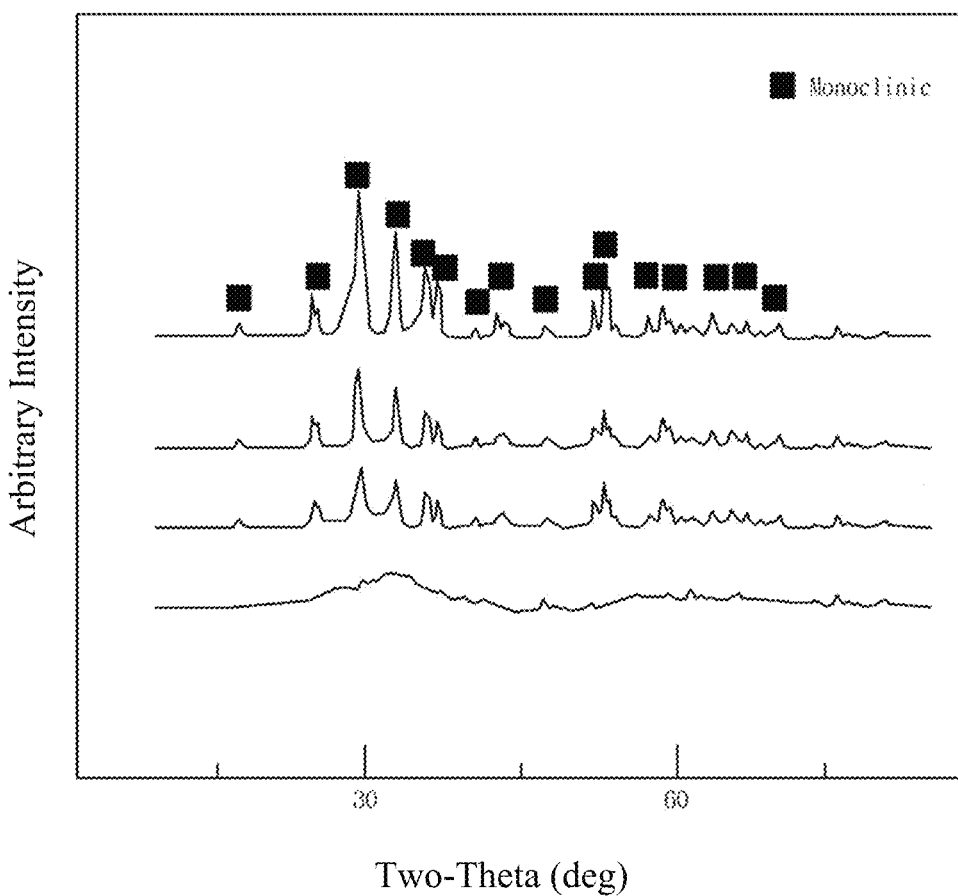
FIGS. 7A-7D are graphs showing changes in the fine structures of the zirconia powder to reaction time according to the present invention.
Figure 8A:
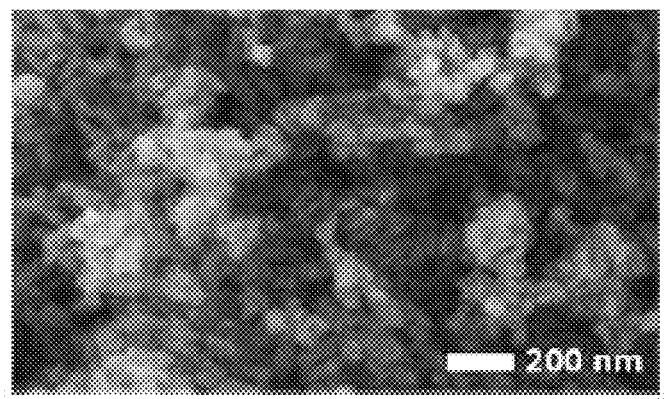
FIGS. 8A-8C and FIGS. 9A-9C are examples of enlarged photographs showing comparison between degrees of surface roughness of a general zirconia slurry sold on the market and the zirconia slurry suggested in the present invention.
Figure 8B:
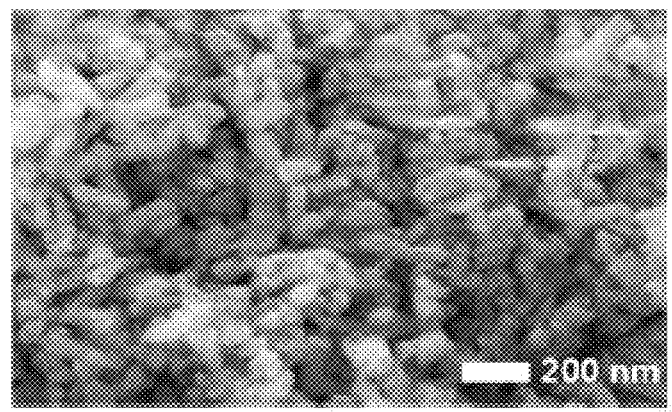
Figure 8C:
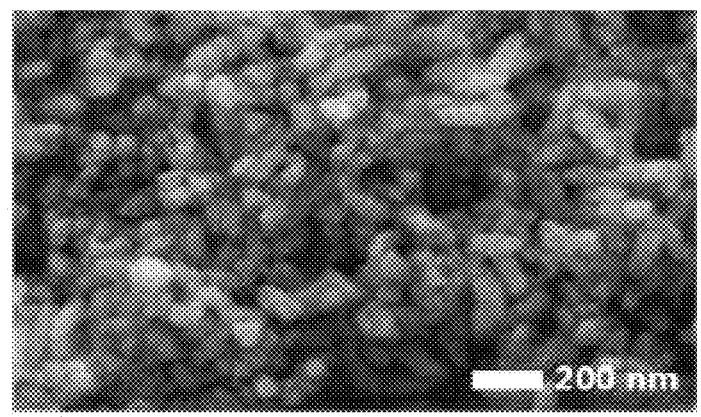
Figure 9A:
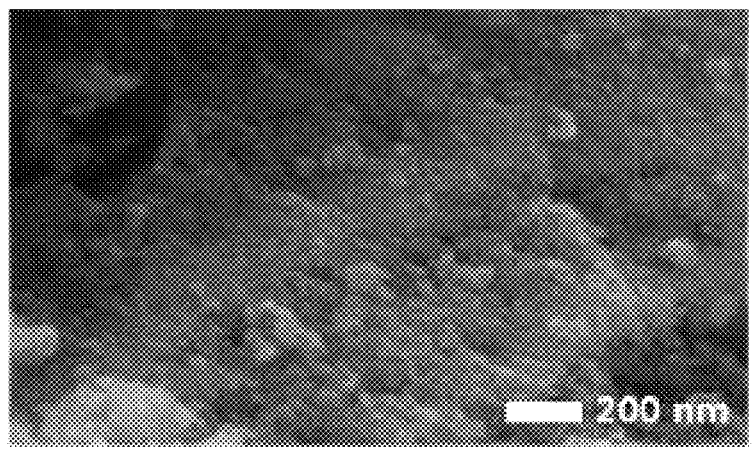
Figure 9B:
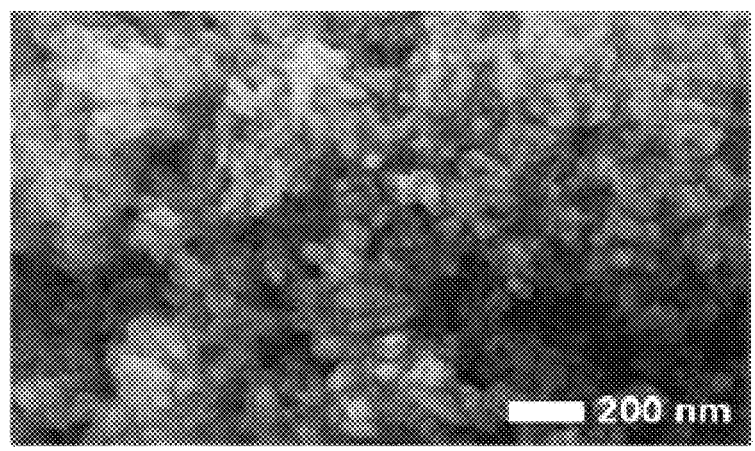
Figure 9C:
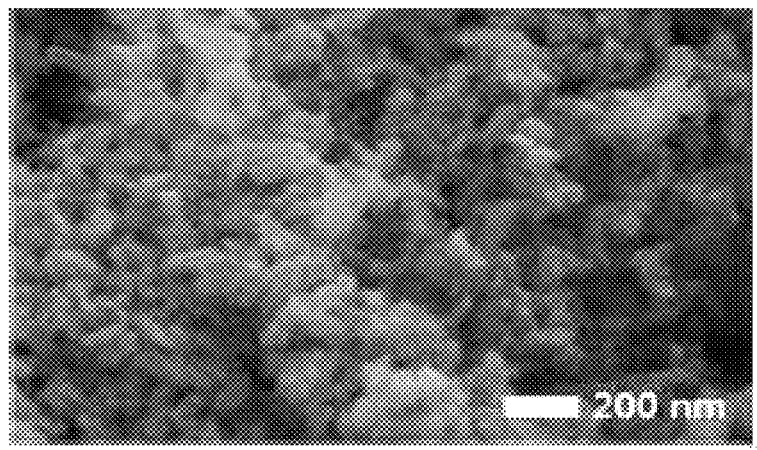

In FIGS. 7A-7D, FIG. 7A is reaction time of 4 h, FIG. 7B is that of 8 h, FIG. 7C is that of 12 h, and FIG. 7D is that of 24 h. If the zirconia powder is synthesized for 8, 12, and 24 h, the respective zirconia powder has monoclinic phases and particle sizes having widths of 30 to 50 nm and lengths of 100 to 200 nm. Contrarily, if the zirconia powder is synthesized for 4 h, it has XRD peak having amorphous phases so that it is hard to recognize the particle sizes thereof. As appreciated from the graph, the longer the reaction time is, the smaller the particle sizes are.

As a result, one of reaction time of 4, 8, 12 and 24 h can be selectively used, but according to the present invention, most desirably, the reaction time of 12 to 24 h, which makes the zirconia powder have the smallest particle sizes, is selected.

On the other hand, the porous surface roughness of the zirconia slurry can be controlled according to concentrations of carbon powder.

According to the present invention, as mentioned above, a temperature of 1200 to 1800° C. is applied to the zirconia mixture to which carbon powder is added to oxidize the carbon powder to a concentration of 10 to 40 wt %.

Comparison and analysis results of an adhesive force between an abutment and a crown according to concentrations of carbon powder are suggested as described in a fourth embodiment, and bond strength experiments are carried out by applying resin cement to samples by area through a tensile strength tester (ASTM F-1044-99). The resin cement was Polyglass of Vericom (Korea).

Fourth Embodiment

| Adhesive strength estimation | | |
| --- | --- | --- |
| | Sample name | Tensile strength(MPa) |
| Control | Bonding area of 7 mm | 0.31 |
| | | 13.63 |
| | | 16.25 |

-continued

Adhesive strength estimation

| | Sample name | Tensile strength(MPa) |
|---|---|---|
| | Bonding area of 14 mm | 27.92 |
| | | 23.44 |
| | | 7.55 |
| | Bonding area of 21 mm | 19.27 |
| | | 6.93 |
| 10 | Bonding area of 7 mm | 20.91 |
| | | 36.35 |
| | | 24.38 |
| | Bonding area of 14 mm | 26.68 |
| | | 21.34 |
| | | 43.08 |
| | Bonding area of 21 mm | 37.04 |
| | | 63.73 |
| | | 70.02 |
| 40 | Bonding area of 7 mm | 59.73 |
| | | 49.48 |
| | | 51.08 |
| | Bonding area of 14 mm | 76.08 |
| | | 39.71 |
| | | 80.58 |
| | Bonding area of 21 mm | 45.75 |
| | | 95.70 |
| | | 88.40 |

<Analysis Table of Adhesive Force Between Abutment and Crown According to Concentrations of Carbon Powder>

As appreciated from the analysis Table, the larger the adhesive area is, the higher the tensile strength is. According to the present invention, contact areas between the abutment and the crown are more extended through the pores of the zirconia slurry than those in the conventional practices, thereby providing the implant having an excellent coupling force. On the other hand, the control sample is not separated at the bonding area of 21 mm thereof, but separated from a jig, thereby recording no value. In this case, the cement is stretched from the sample, while being not separated therefrom. As appreciated from the analysis Table, the sample names 10 and 40 show carbon powder concentrations of 10 wt % and 40 wt % in the zirconia slurry, and it can be checked that the zirconia slurry has the most excellent adhesive force and tensile strength at the carbon powder concentration of 40 wt %.

As a result, carbon powder concentrations of 10 to 40 wt % can be selectively used, but according to the present invention, most desirably, the carbon powder concentration of 40 wt % is used to sinter the zirconia powder.

So as to more finely machine the particle sizes of the zirconia powder constituting the zirconia slurry according to the present invention, on the other hand, the ball mill is made as follows.

Figure 2:
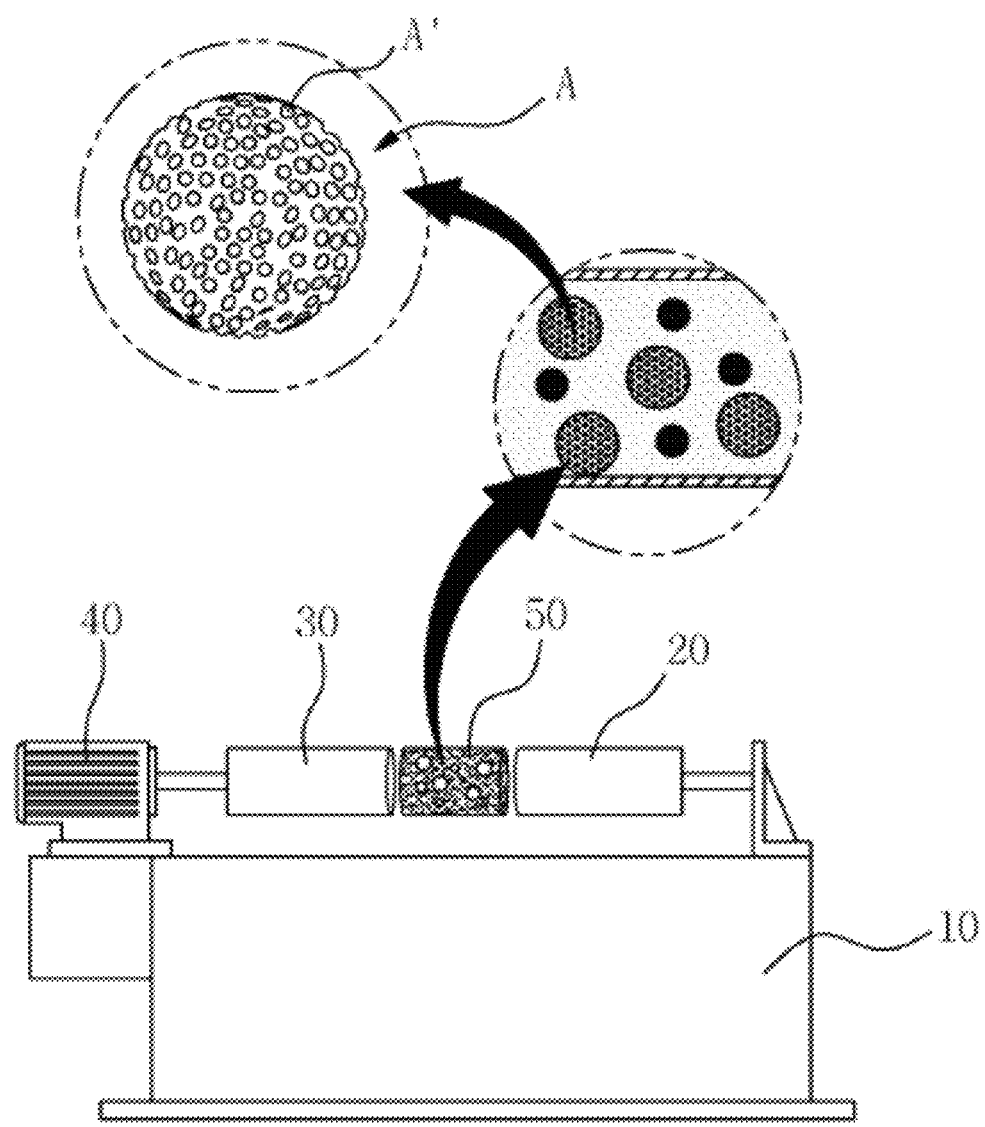
FIG. 2 is a front view showing a ball mill for machining zirconia powder in the method according to the present invention.

FIG. 2 is a front view showing a ball mill for machining zirconia powder in the method according to the present invention.

As shown in FIG. 2, the ball mill used in the present invention includes a frame 10 built on the ground, a pair of pressurizing rollers 20 and 30 disposed on the frame 10 on left and right sides of the frame 10, and a motor 40 connected to any one of the pair of pressurizing rollers 20 and 30 to apply a rotary force to the connected pressurizing roller. A cylindrical machining container 50, in which the zirconia powder, the carbon powder, the organic binder, the dispersing agent, and the solvent constituting the zirconia slurry are stored, is positioned between the pressurizing rollers 20 and 30 and is thus rotated together with the pressurizing rollers 20 and 30 by means of the motor 40, thereby machining the mixture stored in the machining container 50 to the form of a slurry.

Also, the machining container 50 whose internal space is extended in a longitudinal direction thereof according to an amount of slurry machined, so that a plurality of machining containers having different sizes may be prepared according to the capacities of the slurry, and the pressurizing rollers 20 and 30 are slidingly movable horizontally in the left and right sides so that they are adjusted in position according to the sizes of the machining container 50.

Accordingly, the zirconia slurry can be manufactured, irrespective of the amounts machined thereof.

Particularly, the machining container 50 has a plurality of agitating balls A put in the internal space thereof. The agitating balls A have different spherical sizes from each other, and pores A' are formed on the surface of each ball A, thereby providing given roughness. The roughness of the pores A' increases friction coefficients between the agitating balls A and the zirconia mixture, thereby allowing gentle pulverization, and further, the enlarged areas and rough outer shapes of the agitating balls A through the pores A' enable the zirconia powder, the carbon powder, the organic binder, the dispersing agent, and the solvent to be actively moved, so that the agitating balls A having the pores A' play a huge role in producing the zirconia slurry having nanoparticles through strong agitation.

When the zirconia powder, the carbon powder, the organic binder, the dispersing agent, and the solvent are agitated, furthermore, the agitating balls A generate vortexes in various directions from every pore A' to allow the zirconia powder, the carbon powder, the organic binder, the dispersing agent, and the solvent to be more rigidly and closely agitated, and according to another example of the agitating balls A in the present invention, the respective pores A' of each agitating ball A communicate internally with each other to allow the zirconia powder, the carbon powder, the organic binder, the dispersing agent, and the solvent to enter the internal spaces of the agitating balls A, so that the zirconia mixture can be pulverized and agitated one more time in the respective agitating balls A, thereby producing the zirconia slurry having more fine particles rapidly and precisely.

FIGS. 8A-8C and FIGS. 9A-9C are enlarged photographs showing comparison between degrees of surface roughness of a general zirconia slurry sold on the market and the zirconia slurry suggested in the present invention.

Figure 3:
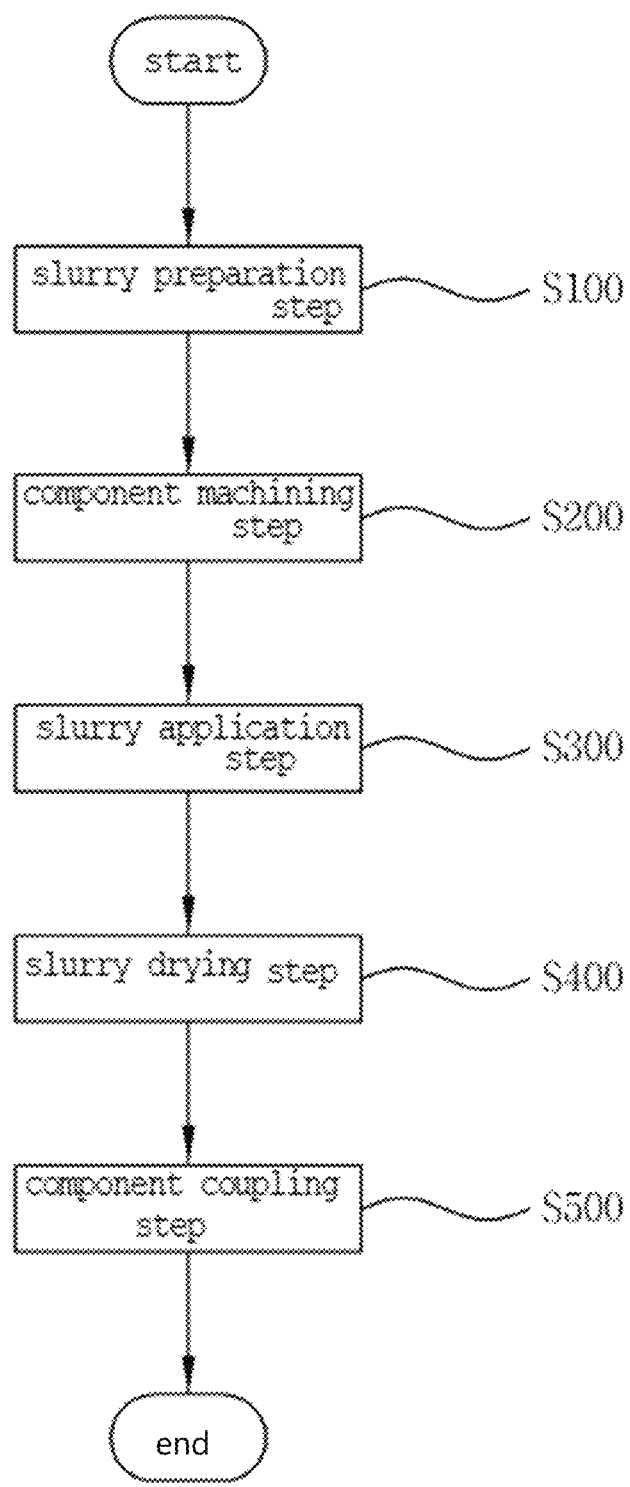
FIG. 3 is a flowchart showing a method for manufacturing an implant to which the zirconia slurry is applied to an abutment and a crown of a ceramic implant according to the present invention.

FIG. 3 is a flowchart showing a method for manufacturing an implant to which the zirconia slurry is applied to an abutment and a crown of a ceramic implant according to the present invention.

As shown in FIG. 3, a method for manufacturing an implant according to the present invention includes: the slurry preparation step (S100) of putting the zirconia slurry produced by means of the ball mill in a storage container; the component machining step (S200) of allowing an inner diameter of a crown to be more enlarged by 0.01 to 0.1 mm than a head of an abutment to ensure a spare space on a coupled surface between the crown and the abutment; the slurry application step (S300) of applying the zirconia slurry to an inner periphery of the crown and the head of the abutment; the slurry drying step (S400) of allowing the crown and the abutment to which the zirconia slurry is applied to be dried at a temperature of 120 to 150° C. for 10 to 20 minutes; and the component coupling step (S500) of press-fitting the head of the abutment to the inner periphery of the crown to allow the abutment and the crown fitted to each other to be coupled to a fixture planted into a patient's alveolar bone.

The slurry preparation step (S100) is carried out by putting the zirconia slurry processed by means of the ball mill in a storage container, and as mentioned above, the method for manufacturing the zirconia slurry includes: the zirconia pulverization step (step S10) of putting zirconia, carbon powder as a foaming agent, and an organic binder in a ball mill and agitating and pulverizing the zirconia, the carbon powder, and the organic binder to allow the zirconia mixture to have nanoparticles; the carbon powder oxidization step (step S20) of heating the zirconia mixture mixed with the carbon powder to a temperature of 1200 to 1800° C. and oxidizing the carbon powder to a concentration of 10 to 40 wt % to allow the porous surfaces to be formed on every particle of the zirconia mixture; and the degreasing step (step S30) of putting a dispersing agent and a solvent in the zirconia mixture having the porous surfaces to make a zirconia solution and removing the organic binder from to the zirconia mixture.

The component machining step (S200) is the step of machining a crown and an abutment. In detail, a titanium material is milled to make the abutment, and a resin or zirconia material is machined to a given shape to make an artificial prosthesis replacing a missing tooth of a patient.

Especially, the component machining step (S200) is carried out by allowing an inner diameter of the crown to be more enlarged by 0.01 to 0.1 mm than a head of the abutment to ensure a spare space on a coupled surface between the crown and the abutment. The zirconia slurry is applied to the spare space formed on the coupled surface, thereby providing a space inducing the press-fitting between the abutment and the crown.

The slurry application step (S300) is carried out by applying the zirconia slurry to an inner periphery of the crown and the head of the abutment, and in this case, the zirconia slurry is applied to a thickness of 0.01 to 0.1 mm to the inner periphery of the crown and the head of the abutment, respectively.

At the slurry application step (S300), the zirconia slurry is painted onto the surfaces of the crown and the abutment by means of a brush, and otherwise, it can be sprayed thereon by means of a pumping member. So as to improve the coupling force between the abutment and the crown through the utilization of the porous surface roughness of the present invention, especially, application flows of the zirconia slurry to the abutment and the crown are different from each other. As a result, friction coefficients on the contacted surfaces between the abutment and the crown can be substantially raised.

In detail, the zirconia slurry is applied toward the upper side of the crown from the inner lower periphery of the crown, thereby allowing porous surface roughness thereof to be enlargedly distributed toward the upper side of the crown from the inner lower periphery of the crown, and contrarily, the zirconia slurry is applied toward the lower side of the abutment from the top of the head of the abutment, thereby allowing porous surface roughness thereof to be enlargedly distributed toward the lower side of the abutment from the top of the head of the abutment.

Of course, the present invention is not limited to the application directions as mentioned above. For example, the zirconia slurry is applied toward the lower side of the crown from the inner upper periphery of the crown, thereby allowing porous surface roughness thereof to be enlargedly distributed toward the lower side of the crown from the inner upper periphery of the crown, and contrarily, the zirconia slurry is applied toward the upper side of the abutment from the bottom of the head of the abutment, thereby allowing porous surface roughness thereof to be enlargedly distributed toward the upper side of the abutment from the bottom of the head of the abutment. Accordingly, the application flows of the zirconia slurry to the abutment and the crown can be freely changed according to a worker's selection.

The slurry drying step (S400) is the step of allowing the components of the implant to be dried at an environment providing a given temperature for given time. Typically, zirconia is one of a variety of ceramics, and for example, the ceramics have high absorptivity so that they can be liable to crack due to surrounding environments and drastic temperature changes.

In detail, foods having various temperatures are taken in a human body's mouth, and through the foods, the zirconia slurry applied between the crown and the abutment may crack. So as to completely solve such a problem, the zirconia slurry should be subjected to a heat treatment to allow the porous surfaces thereof to be solidly attached to the crown and the abutment.

So as to prevent the ceramics from cracking, accordingly, the crown and the abutment to which the zirconia slurry is applied are put into an oven and are dried at a temperature of 120 to 150° C. for 10 to 20 minutes, thereby rapidly evaporating the water contained in the zirconia slurry and allowing the zirconia powder and the carbon powder of the zirconia slurry to be strongly attached to the crown and the abutment through the drastic drying.

The component coupling step (S500) is carried out by press-fitting the head of the abutment to the inner periphery of the crown to allow the abutment and the crown fitted to each other to be coupled to a fixture planted into a patient's alveolar bone.

First, the inner diameter of the crown is more enlarged by 0.01 to 0.1 mm than the head of the abutment to ensure the spare space on the coupled surface between the crown and the abutment, but the zirconia slurry is applied to a thickness of 0.01 to 0.1 mm to the inner periphery of the crown and the head of the abutment, respectively, to form the porous surfaces, so that the spare space becomes insufficient by a maximum thickness of 0.1 mm.

In this state, the crown and the abutment are press-fitted to each other, so that they can be integrally formed with each other, without any separate member. As appreciated from the slurry application step (S300), moreover, the zirconia slurry is applied to the coupled surfaces between the abutment and the crown in reverse directions to each other, so that the crown and the abutment can engage with each other with an improved coupling force.

Next, an explanation on a method for manufacturing a laminate through the application of the zirconia slurry of the present invention will be given below.

So as to improve an outer shape of a tooth with an esthetic purpose, generally, a laminate is made by at least deleting only the labial surface of an enamel of a front tooth and by then bonding a porcelain prosthesis to the labial surface through a hybrid composite resin.

A general method for manufacturing the laminate includes the steps of: performing local anesthesia around a surgery tooth to delete the tooth; making an impression of the tooth through addition silicone; making a temporary tooth and attaching the temporary tooth to the deleted tooth; completely making a prosthesis through a dental technique; fitting the prosthesis to the tooth to apply 10% by weight of hydrofluoric acid to the tooth and the inner surface of the prosthesis for about 90 seconds so as to enhance a bonding force; completely attaching the prosthesis to the tooth through an adhesive resin; and performing occlusal adjustment.

In case of the laminate having such a surgery procedure, relatively long time, that is, about 10 to 20 minutes are needed each tooth to attach a porcelain veneer to the tooth, and further, the laminate has various side effects and aftereffects such as escape of the porcelain veneer due to poor contact of cement, a partial or whole fracture of the porcelain veneer, discoloration of gap between the veneer and the tooth, dentin hypersensitivity caused by excessive deletion of tooth, and so on. Under such reasons, the present invention provides a method for improving durability of the veneer itself, enhancing a coupling force between the tooth and the veneer, and performing fast coupling.

A method for manufacturing a laminate according to the present invention includes: the slurry preparation step (S100) of putting the zirconia slurry made by means of the ball mill in a storage container; the component machining step (S200) of putting a melted ceramic material into a mold to make a veneer; the slurry application step (S300) of applying the zirconia slurry to an inner surface of the veneer; the slurry drying step (S400) of allowing the veneer to which the zirconia slurry is applied to be dried at a temperature of 120 to 150° C. for 10 to 20 minutes; and the component coupling step (S500) of applying a composite resin to a patient's tooth to attach the veneer to the tooth.

The slurry preparation step (S100) is carried out in the same manner as in the above-mentioned method for manufacturing the implant having the crown and the abutment, and a detailed explanation on the slurry preparation step (S100) in the method for manufacturing the laminate according to the present invention will be avoided.

The component machining step (S200) is the step of cutting and machining a ceramic material to a given shape or putting a melted ceramic material into an injection mold to allow the ceramic material to a shape compensating for the patient's damaged tooth.

The slurry application step (S300) is the step of applying the zirconia slurry to an inner surface of the veneer, and so as to allow the zirconia slurry to be gently applied to the inner surface of the veneer, the method according to the present invention further includes the step of putting the zirconia slurry made by the ball mill in the storage container prepared separately. In more detail, the pressurizing forces of the pair of pressurizing devices 20 and 30 of the ball mill are released to isolate the machining container 50 from the ball mill, and after that, the agitated zirconia slurry in the machining container 50 is poured into the storage container.

Further, the storage container is classified into a paint container and a spray container according to application methods of the zirconia slurry to the veneer. The paint container is open on top thereof to apply the zirconia slurry stored therein to a brush, and the spray container has a shape of a sprayer on top thereof.

Particularly, the paint container and the spray container include at least one or more zirconia balls having various sizes, like the agitating balls A of the ball mill, accommodated therein. For example, if the zirconia slurry having the nanoparticles through the ball mill is stored into the storage container for long hours, its particles sink in the storage container, and accordingly, they have to shake. At the time when the storage container shakes to mix the particles of the zirconia slurry, the agitating balls A accommodated in the storage container shake together with the zirconia slurry to allow the zirconia slurry sinking in the storage container to be mixed well.

The slurry application step (S300) is carried out by applying the zirconia slurry to the inner surface of the veneer by means of painting or spraying, and in this case, the zirconia slurry is applied to a thickness of 0.1 to 0.5 mm to the inner surface of the veneer by means of the brush or the pumping member having a shape of a sprayer.

At the slurry application step (S300), the zirconia slurry is applied through the brush toward the lower side of the veneer from the top end of the veneer, and otherwise, the zirconia slurry is applied through the pumping member toward the lower side of the veneer from the top end of the veneer, thereby being enlargedly distributed toward the lower side of the veneer. Of course, the present invention is not limited to the application directions as mentioned above. For example, the zirconia slurry is applied through the brush toward the upper side of the veneer from the bottom of the veneer, and otherwise, the zirconia slurry is applied through the pumping member toward the upper side of the veneer from the bottom of the veneer, thereby being enlargedly distributed toward the upper side of the veneer. Accordingly, the application flows of the zirconia slurry to the veneer can be freely changed according to a worker's selection.

The slurry drying step (S400) is the step of allowing the veneer to which the zirconia slurry is applied to be dried at a temperature of 120 to 150° C. for 10 to 20 minutes, and generally, the veneer is made by cutting and machining a ceramic material to a given shape or putting a melted ceramic material into an injection mold to machine the ceramic material to a given shape. For example, the ceramics have high absorptivity so that they can be liable to crack due to surrounding environments and drastic temperature changes. So as to prevent the ceramics from cracking, accordingly, the veneer to which the zirconia slurry is applied is put into an oven and is dried at a temperature of 120 to 150° C. for 10 to 20 minutes, thereby rapidly evaporating the water contained in the zirconia slurry and allowing the zirconia powder and the carbon powder of the zirconia slurry to be strongly attached to the veneer through the drastic drying.

The component coupling step (S500) is carried out by applying a composite resin to a patient's tooth to attach the veneer to the tooth. At this step, in more detail, the labial surface of the patient's surgery tooth is deleted, and the composite resin is applied to the whole surface of the deleted tooth to attach the veneer to which the zirconia slurry is applied thereto.

On the other hand, the composite resin is applied in one direction to the surgery tooth of the patient in the same manner as the zirconia slurry applied to the inner surface of the veneer, thereby being enlargedly distributed to the tooth. In detail, the composite resin is sprayed toward the lower side of the tooth from the top of the tooth, thereby being enlargedly distributed to the lower side of the tooth, and contrarily, the composite resin is sprayed toward the upper side of the tooth from the bottom of the tooth, thereby being enlargedly distributed to the upper side of the tooth. Desirably, the application flow of the composite resin to the tooth is in the opposite direction to that of the zirconia slurry to the veneer.

Like this, the zirconia slurry is applied toward the lower side of the veneer from the top end of the veneer at the slurry application step (S300), thereby being enlargedly distributed toward the lower side of the veneer, and the composite resin is sprayed toward the upper side of the tooth from the bottom of the tooth at the component coupling step (S500), thereby being enlargedly distributed to the upper side of the tooth, so that the application flows to the veneer and the tooth are reverse to allow roughness angles of the veneer and the tooth to engage with each other, thereby improving the coupling force therebetween.

On the other hand, coupling forces are measured according to porous surface roughness application directions of zirconia slurry, and the experimental results for the coupling forces are as follows.

Comparison Example 1

A sample with a zirconia slurry applied in a typical method to a general zirconia block, wherein the zirconia slurry consists of hydrofluoric acid, sulfuric acid, catalyst, and methanol.

Comparison Example 2

A sample with a zirconia slurry applied to a general zirconia block in respective reverse directions to each other, wherein the zirconia slurry of the present invention consists of the zirconia powder, the carbon powder, the organic binder, the dispersing agent, and the solvent.

Figure 10:
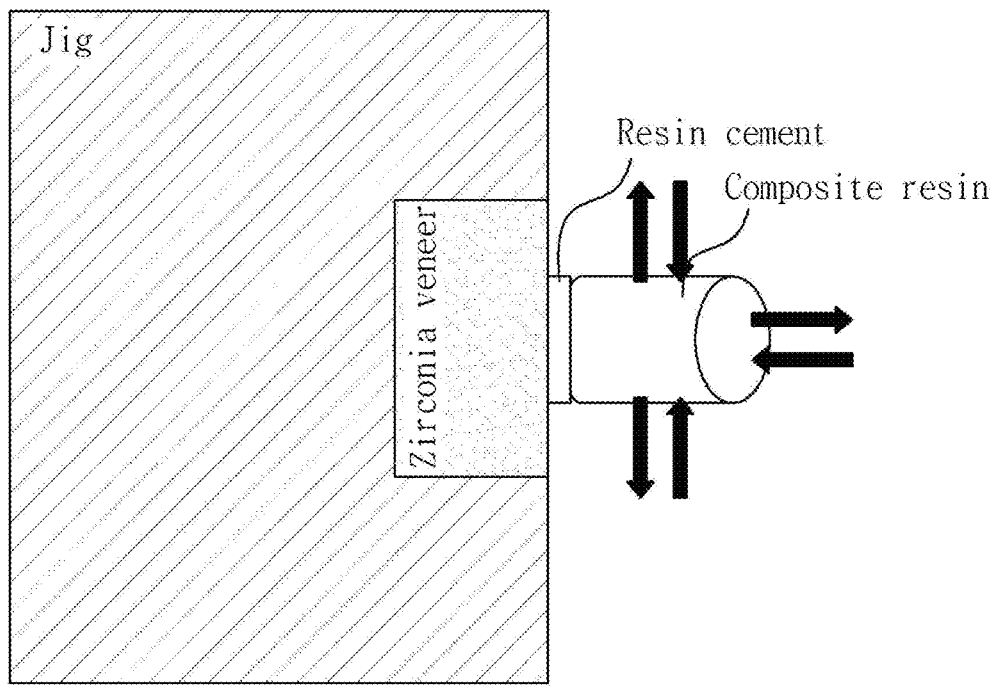
FIG. 10 shows an experimental method for measuring coupling forces according to surface treatment methods.
Figure 11:
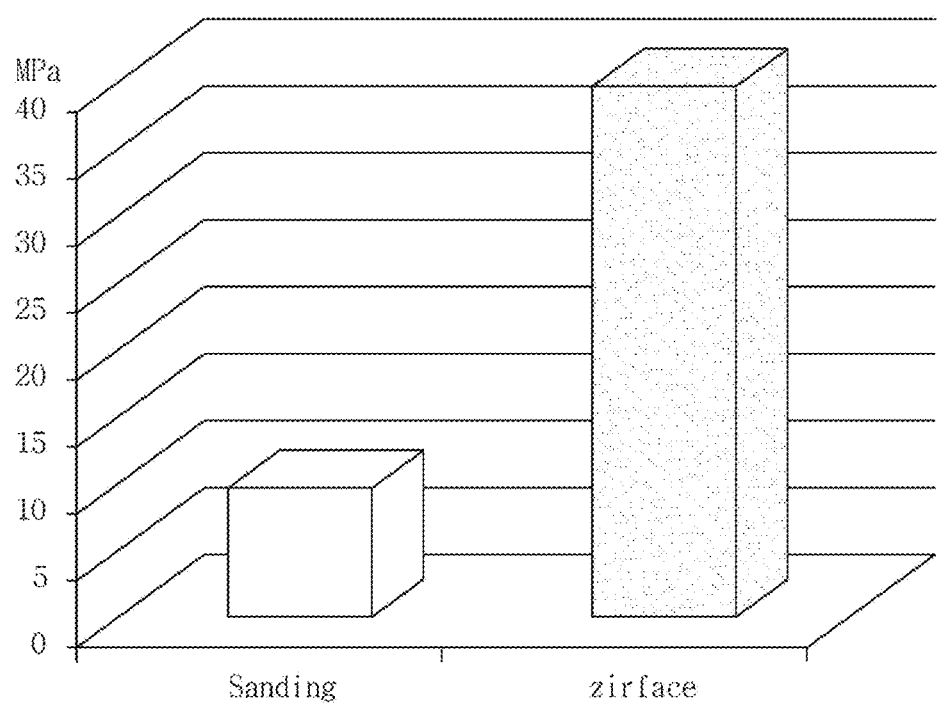
FIG. 11 shows a comparison graph for the measurement results of the coupling forces according to surface treatment methods.

After the samples of the Comparison examples 1 and 2 were seated onto jigs, as shown in FIG. 10, a composite resin was attached to the samples, and external forces were applied to the samples, thereby measuring the coupling forces.

As appreciated from the comparison graph, the zirconia block coupled through a general surface treatment agent and sanding in the Comparison example 1 have a coupling force of about 5 to 10 MPa, and contrarily, the present invention in the Comparison example 2, in which the zirconia slurry having the zirconia particles having various sizes is applied to the veneer in a different direction from an application direction to the tooth, have a coupling force of about 35 to 40 MPa. As a result, it is appreciated that the coupling force in the Comparison example 2 is more improved by three times than that in the Comparison example 1.

Under the above-mentioned configuration of the present invention, the zirconia slurry having the nanoparticles is applied to the coupled surfaces of the components constituting the implant to form the porous surfaces, so that the coupling force of the components can be drastically increased by means of their increased friction and surface areas.

Particularly, the zirconia having excellent human affinity is selected from the ceramic materials, and it is also machined by means of the ball mill to the form of powder having the nanoparticles, so that bio-convergence can be greatly improved and the surface roughness can be more finely applied to the components of the implant.

Further, the components of the zirconia slurry according to the present invention, such as zirconia powder, carbon powder, binder, dispersing agent, distilled water, and solvent, give no harm to the human body, and above all, the porous surfaces are formed on every particle of the zirconia powder by means of the hydrothermal synthesis, thereby more effectively allowing the porous surface roughness to be adjusted to fine levels.

Also, the zirconia slurry is applied to the coupled surfaces of the components constituting the implant at various angles to form different surface roughness flows, thereby improving the coupling force of the components, and even if long time is elapsed after the surgery, the separation of the zirconia slurry from the patient's mouth can be prevented to provide permanent management. Further, as the components of the implant are dried at a temperature of 120 to 150° C.

for 10 to 20 minutes, cracks, which are likely to occur on the implant components made of the ceramic material weak to water, can be completely prevented.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A method for manufacturing a zirconia slurry for forming porous surfaces on an abutment and a crown of an implant,
the method comprising:
a zirconia pulverization step of putting zirconia,
carbon powder as a foaming agent, and
an organic binder in a ball mill and agitating and pulverizing the zirconia,
the carbon powder, and
the organic binder to allow a zirconia mixture to have nanoparticles;
a carbon powder oxidization step of heating the zirconia mixture mixed with the carbon powder to a temperature of 1200 to 1800 degree C. and oxidizing the carbon powder to a concentration of 10 to 40 wt % to allow the porous surfaces to be formed on particles of the zirconia mixture; and
a degreasing step of putting a dispersing agent and a solvent in the zirconia mixture having the porous surfaces to make a zirconia solution and removing the organic binder from the zirconia mixture.

2. The method according to claim 1,
wherein the zirconia pulverization step comprises:
the powder preparation step of selecting one from zirconium acetate hydroxide,
zirconium nitrate, and
zirconium chloride and pulverizing the selected one by the ball mill;
a distilled water preparation step of adding double distilled water having a deionized process in an internal space of an autoclave used for hydrothermal synthesis; and
a powder dissolution step of adjusting a temperature of the autoclave to which the distilled water is added to a temperature of 90 to 100 degree C.,
putting the zirconia powder and a precipitation agent into the autoclave, and
dissolving the zirconia powder for two to four hours.

3. The method according to claim 2, wherein the precipitation agent is one selected from NaOH and KOH.

4. A method for manufacturing the implant with the zirconia slurry manufactured according to claim 1 so as to form the porous surfaces on the abutment and the crown of the implant,
the method comprising: the slurry preparation step of putting the zirconia slurry in a storage container;
the component machining step of allowing an inner diameter of the crown to be more enlarged by 0.01 to 0.1 mm than a head of the abutment to ensure a spare space on a coupled surface between the crown and the abutment;
a slurry application step of applying the zirconia slurry to an inner periphery of the crown and the head of the abutment;

the slurry drying step of allowing the crown and the abutment to which the zirconia slurry is applied to be dried at a temperature of 120 to 150.degree C. for 10 to 20 minutes; and the component coupling step of press-fitting the head of the abutment to the inner periphery of the crown to allow the abutment and the crown fitted to each other to be coupled to a fixture planted into a patient's alveolar bone.

5. The method according to claim 4, wherein the ball mill for pulverizing the zirconia powder comprises a machining container and at least one or more having different diameters disposed in the machining container, and the agitating balls have the porous surfaces to allow the zirconia powder to be machined to nanoparticles sizes.

6. The method according to claim 4, wherein at the slurry application step, the zirconia slurry is applied toward a lower side of the crown from an inner upper periphery of the crown, thereby being enlargedly distributed toward the lower side of the crown from the inner upper periphery of the crown, and the zirconia slurry is applied toward an upper side of the abutment from the bottom of the head of the abutment, thereby being enlargedly distributed toward the upper side of the abutment from the bottom of the head of the abutment, so that the application flows of the zirconia slurry to the abutment and the crown are in reverse directions to each other.

* * * * *